(12) United States Patent
Behlmaier

(10) Patent No.: US 8,844,534 B2
(45) Date of Patent: Sep. 30, 2014

(54) TRACHEAL TUBE WITH LUMEN FOR TRACHEAL PRESSURE MEASUREMENT AND TECHNIQUE FOR USING THE SAME

(75) Inventor: Mark R. Behlmaier, Erie, CO (US)

(73) Assignee: Covidien LP, Mansfield, MA (US)

( * ) Notice: Subject to any disclaimer, the term of this patent is extended or adjusted under 35 U.S.C. 154(b) by 1468 days.

(21) Appl. No.: 12/495,326

(22) Filed: Jun. 30, 2009

(65) Prior Publication Data
US 2010/0326446 A1    Dec. 30, 2010

(51) Int. Cl.
*A61M 16/04*    (2006.01)

(52) U.S. Cl.
CPC ......... *A61M 16/044* (2013.01); *A61M 16/0459* (2014.02); *A61M 16/0443* (2014.02); *A61M 16/0434* (2013.01)
USPC .................................................. 128/207.15

(58) Field of Classification Search
USPC .......................... 128/207.14–207.18, 200.26; 604/96.01–103.08, 516; 606/191–197
See application file for complete search history.

(56) References Cited

U.S. PATENT DOCUMENTS

| | | | |
|---|---|---|---|
| 3,931,822 A | 1/1976 | Marici | |
| 4,285,340 A | 8/1981 | Gezari et al. | |
| 4,344,436 A | 8/1982 | Kubota | |
| 4,526,196 A | 7/1985 | Pistillo | |
| 4,552,558 A | 11/1985 | Muto | |
| 4,565,194 A | 1/1986 | Weerda et al. | |
| 4,617,015 A | 10/1986 | Foltz | |
| 4,630,606 A | 12/1986 | Weerda et al. | |
| 4,813,431 A * | 3/1989 | Brown | 600/561 |
| 4,850,969 A * | 7/1989 | Jackson | 604/96.01 |
| 4,886,059 A | 12/1989 | Weber | |
| 4,898,168 A | 2/1990 | Yule | |
| 5,218,970 A | 6/1993 | Turnbull et al. | |
| 5,235,973 A | 8/1993 | Levinson | |
| 5,285,778 A | 2/1994 | Mackin | |
| 5,361,753 A | 11/1994 | Pothmann et al. | |
| 5,400,771 A | 3/1995 | Pirak et al. | |
| 5,445,144 A | 8/1995 | Wodicka et al. | |
| 5,487,383 A | 1/1996 | Levinson | |
| 5,487,731 A | 1/1996 | Denton | |
| 5,497,768 A | 3/1996 | Lomholt | |
| 5,546,935 A | 8/1996 | Champeau | |
| 5,560,351 A | 10/1996 | Gravenstein et al. | |
| 5,591,130 A | 1/1997 | Denton | |
| 5,740,796 A | 4/1998 | Skog | |

(Continued)

FOREIGN PATENT DOCUMENTS

WO    9422518    10/1994

OTHER PUBLICATIONS

International Search Report PCT/US2010/038778, 3 pages, mailed Sep. 13, 2010.

(Continued)

*Primary Examiner* — (Jackie) Tan-Uyen T Ho
*Assistant Examiner* — Peter S Vasat
(74) *Attorney, Agent, or Firm* — Fletcher Yoder PC

(57) ABSTRACT

According to various embodiments, a tracheal tube may include a pressure monitoring lumen configured to provide information related to the pressure in the tracheal space. By measuring pressure in the lumen, a tracheal pressure may be estimated. The pressure monitoring lumen may be in fluid communication with a pressure transducer that provides pressure measurements. An opening of the lumen may be covered with a distal shoulder of an inflatable cuff.

21 Claims, 4 Drawing Sheets

(56) References Cited

U.S. PATENT DOCUMENTS

| | | | |
|---|---|---|---|
| 5,752,921 | A | 5/1998 | Orr |
| 5,819,723 | A | 10/1998 | Joseph |
| 5,885,248 | A | 3/1999 | Denton |
| 5,906,204 | A | 5/1999 | Beran et al. |
| 6,315,739 | B1 | 11/2001 | Merilainen et al. |
| 6,530,898 | B1 | 3/2003 | Nimkar et al. |
| 6,647,984 | B1 | 11/2003 | O'Dea |
| 6,705,319 | B1 | 3/2004 | Wodicka et al. |
| 6,820,618 | B2 | 11/2004 | Banner et al. |
| 6,918,391 | B1 | 7/2005 | Moore |
| 2002/0072680 | A1* | 6/2002 | Schock et al. ............... 600/486 |
| 2005/0039754 | A1 | 2/2005 | Simon |
| 2005/0274382 | A1* | 12/2005 | Lomholt ................ 128/207.15 |
| 2005/0279360 | A1 | 12/2005 | Wei |
| 2007/0299357 | A1 | 12/2007 | Villegas |
| 2008/0110468 | A1 | 5/2008 | Nelson et al. |
| 2008/0210235 | A1 | 9/2008 | Field et al. |
| 2009/0038620 | A1 | 2/2009 | Efrati |

OTHER PUBLICATIONS

Lomholt, N., A Device for Measuring the Lateral Wall Cuff Pressure of Endotracheal Tubes, Acta Anaesthesiologica Scandinavica, Dec. 1992, pp. 775-778, Issue 36.

Pollard, Richard. J. MD et al., Endotracheal Tube Location Verified Reliably by Cuff Palpation, Anesthesia and Analgesia, 1995, pp. 135-138.

Cardoso, Monica M. S. C. MD et al., Portable Devices Used to Detect Endotracheal Intubation During Emergency Situations: A Review, Critical Care Medicine, May 1998, pp. 957-964, vol. 26, Issue 5.

Valentino, Joseph MD et al., Utility of Portable Chest Radiographs as a Predictor of Endotracheal Tube Cuff Pressure, Otolaryngology-Head and Neck Surgery, Jan. 1999, pp. 51-56, vol. 1, Issue 120.

Guttmann, Josef PhD et al., Continuous Calculation of Intratracheal Pressure in the Presence of Pediatric Endotracheal Tubes, Critical Care Medicine, Apr. 2000, pp. 1-21, vol. 28, Issue 4.

Karasawa, Fujio. MD et al., Profile Soft-Seal Cuff, a New Endotracheal Tube, Effectively Inhibits an Increase in the Cuff Pressure through High Compliance Rather than Low Diffusion of Nitrous Oxide, Anesthesia and Analgesia, Dec. 2001, pp. 140-144, Issue 92.

Sondergaard, Soren. et al., Direct Measurement of Intratracheal Pressure in Pediatric Respiratory Monitoring, Pediatric Research, Dec. 2002, vol. 51, No. 3.

Dullenkopf, A. et al., Air Leakage Around Endotracheal Tube Cuffs, European Journal of Anaesthesiology, Dec. 2004, pp. 448-453, Issue 21.

Horisberger, T. et al., Measurement of Tracheal Wall Pressure: A Comparison of Three Different in Vitro Techniques, Journal of the Association of Anaesthetists of Great Britain and Ireland, Dec. 2008, pp. 418-422, Issue 63.

Khazin, Vadim MD et al., Gastroesophageal Regurgitation during Anesthesia and Controlled Ventilation with Six Airway Devices, Journal of Clinical Anesthesia, Dec. 2008, pp. 508-513, Issue 20.

Orr, Joseph A., Tracheal Pressure Controller for Ventilators, National Institute Of Allergy And Infectious Diseases, Jun. 2010, pp. 1-7.

Sheridan ETCO2 Uncuffed Endotracheal Tubes, Monitoring Lumen Tubes, Hudson RCI, 2010, pp. 1-2.

U.S. Appl. No. 12/477,636, filed Jun. 3, 2009, Lockette E. Wood.

* cited by examiner

TRACHEAL TUBE WITH LUMEN FOR TRACHEAL PRESSURE MEASUREMENT AND TECHNIQUE FOR USING THE SAME

BACKGROUND

The present disclosure relates generally to medical devices and, more particularly, to airway devices, such as tracheal tubes.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

To seal these types of tracheal tubes, an inflatable cuff may be associated with the tubes. When inflated, the cuff generally expands into the surrounding trachea to seal the tracheal passage around the tube to facilitate the controlled delivery of gases via a medical device (e.g., through the tube). For intubated patients, the flow rate and volume of gas transferred into the lungs, which may vary according to the condition of each patient, may be controlled by the settings of a ventilator. One factor that is used to determine the ventilator settings may be an airway pressure measurement, which is typically obtained by measuring the pressure along the breathing circuit (e.g., medical tubing connecting the tracheal tube to the ventilator) at a point outside the patient. Airway pressure measured in the breathing circuit at a point outside the patient may be a useful surrogate for the pressure in the lungs, which may in turn be used for calculating a number of ventilator settings, for example settings involving pressure limits.

However, in circumstances where the internal diameter of the tracheal tube is diminished, for example through the buildup of mucosal secretions that may partially block the airflow passage of the tracheal tube, the lung pressure may be lower than the airway pressure measurement taken outside the patient. Accordingly, an airway pressure measurement may not always serve as a reliable substitute for lung pressure measurements.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

Figure 1:
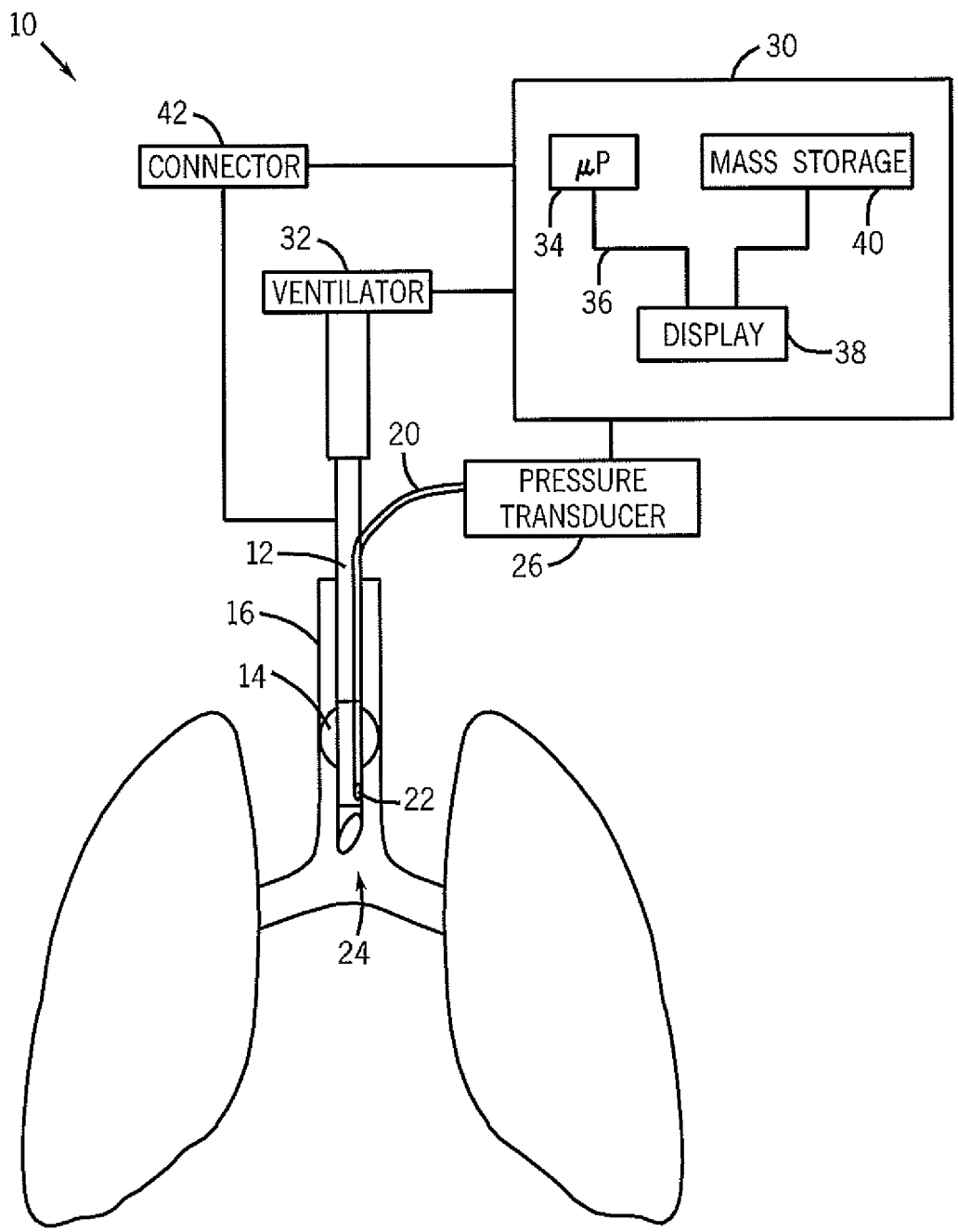
FIG. 1 illustrates a system including an endotracheal tube with a pressure transducer according to embodiments of the present techniques.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Because obtaining direct measurements of the pressure in the internal space of the lungs is difficult, clinicians and respiratory specialists may use surrogate measurements of pressure along various points of breathing circuit or the patient's airway to estimate the lung pressure. The lung pressure estimates may then be used to determine the efficacy of the ventilation (e.g., the dynamic intrapulmonary compliance) and, in some cases, may be used to control the settings of a ventilator, either manually or automatically, to provide a clinical benefit to the patient.

Airway pressure may be estimated by using measurements of pressure taken along various points of the breathing circuit that are proximal to the tracheal tube. For example, such measurements may be used to assess a patient's work of breathing, which may include the airway resistance during movement of air into and out of the lungs. If the work of breathing of the patient increases, clinicians may assess whether the increase is due to increased airway resistance in the patient (e.g., stiffened lung tissue, which may be related to a clinical condition) or increased resistance in the tracheal tube due to buildup of biofilms on the inner diameter of the tube. Because airway pressure measurements taken proximal to the tracheal tube may not provide information about resistance built up distally, either in the patient or in the tube, trachea pressure measurements may provide information to the clinician about airway or tube-originated resistance. Trachea pressure may refer to pressure in the airway space below the cuff or near the distal tip of the cuff. With this information, when a patient's work of breathing increases, the clinician knows if it is due a change in the diameter of the tracheal tube or a change in the patient's respiratory system. If the resistance buildup is at least in part due to the tracheal tube, he may take action to suction secretions or increase the peak inspiratory pressure to overcome the increased resistance in the tracheal tube. If the work of breathing increase is due to the patient's respiratory system, he may deliver medication to the patient or change the ventilator settings. Tube-based increased work of breathing may be associated with patients who are relatively healthier than patients whose airway resistance has increased the work of breathing. In addition, isolating the resistance to the tube may alert caregivers to kinks or other mechanical changes in the shape of the tube. Using such information may allow the clinician to more accurately assess when a patient is ready to come off of ventilator-assisted breathing.

In particular, because the internal diameter of tracheal tube may change during the time that the patient is intubated, for example through the buildup of patient secretions within the tube, measurements taken upstream of the tracheal tube in the breathing circuit may not be reliable for estimating pressure in the lungs. In certain embodiments, a measurement of tracheal pressure may be used as a surrogate for lung pressure or other pulmonary pressure measurements. The tracheal space is contiguous with the lung space, and tracheal pressure may be a more reliable measurement than measurements taken far upstream along the breathing circuit. Direct measurements may be difficult to obtain during long-term monitoring situations, because pressure transducers incorporated into the distal end of a tracheal tube may become covered in mucus or secretions, resulting in unreliable measurements.

Accordingly, the disclosed embodiments provide a more accurate method and reliable system for determining trachea pressure by providing a pressure monitoring lumen associated with the tracheal tube. The pressure monitoring lumen may be separated from the tracheal space by a substantially gas-impermeable membrane. The membrane may be part of the cuff structure such that a shoulder portion of the cuff that is normally attached to an unbroken surface of the tube may be stretched over an opening formed in the tube that is in fluid communication with the pressure monitoring lumen. The materials from which inflatable cuffs are typically formed are substantially impermeable to most respiratory gases and are suitable for use in covering the opening in the pressure monitoring lumen as provided. It is contemplated that, to determine information about the pressure in the tracheal space, the opening may be located distally of the inflatable region of the cuff and may be covered by a distal shoulder of the cuff.

The membrane (e.g., a portion of the cuff shoulder) interacts with the tracheal space and affects the pressure in the lumen. An increase in the trachea pressure may exert a corresponding increased pressure on the membrane, for example by pushing the membrane into the opening of the pressure monitoring lumen and causing the pressure inside the lumen to increase. Similarly, a drop in pressure in the tracheal space may cause the pressure in the pressure monitoring lumen to decrease. Accordingly, pressure measurements taken on the gas pressure in the pressure monitoring lumen may serve as a substitute for direct measurement of pressure in the trachea.

In certain presently contemplated embodiments, the calculated trachea pressure based on the pressure in the pressure monitoring lumen may be used to evaluate, adjust, or correct airway pressure values obtained along the breathing circuit or tracheal pressure values. For example, if the estimate of trachea pressure based on pressure monitoring lumen varies significantly from the airway pressure measured upstream at a point closer to the ventilator, a clinician may be able to determine that the tracheal tube is blocked with secretions or other buildup, or that some other condition has developed, which may involve action by the clinician.

In embodiments, the disclosed tracheal tubes, systems, and methods may be used in conjunction with any appropriate medical device, including without limitation a feeding tube, an endotracheal tube, a tracheotomy tube, a circuit, an airway accessory, a connector, an adapter, a filter, a humidifier, a nebulizer, nasal cannula, or a supraglottic mask/tube. The present techniques may also be used to monitor any patient benefiting from mechanical ventilation, e.g., positive pressure ventilation. Further, the devices and techniques provided herein may be used to monitor a human patient, such as a trauma victim, an intubated patient, a patient with a tracheotomy, an anesthetized patient, a cardiac arrest victim, a patient suffering from airway obstruction, or a patient suffering from respiratory failure.

FIG. 1 shows an exemplary tracheal tube system 10 that has been inserted into a patient's trachea. The system 10 includes a tracheal tube 12, shown here as endotracheal tube, with an inflatable balloon cuff 14 that may be inflated to form a seal against tracheal walls 16. The tracheal tube 12 may also include a pressure monitoring lumen 20 that has an opening 22 at the distal end of the lumen 20. The opening 22 is covered by a portion of the cuff shoulder, discussed below, such that the lumen 20 is separated from the tracheal space 24 by a gas-impermeable membrane. A proximal portion of the pressure monitoring lumen may be in fluid communication with a pressure transducer 26, which in turn may communicate with a monitor 30. The pressure transducer 26 may be located outside the tracheal tube 12 or may be disposed in the lumen 20. In one embodiment, a mechanical pressure sensor may be used instead of or in addition to a pressure transducer 26. For example, a mechanical strain gauge sensor may be coupled to an analog or digital display, such as on a clip-on display associated with the tube 12.

When the system 10 includes devices that facilitate positive pressure ventilation of a patient, such as ventilator 32, any ventilator may be used, such as those available from Nellcor Puritan Bennett LLC. As noted, the system may also include monitor 30 that may be configured to implement embodiments of the present disclosure. The monitor 30 may be a stand-alone device or may be coupled to another patient monitor or to the ventilator 32. The monitor 30 may include a microprocessor 34 coupled to an internal bus 36 and a display 38. Regardless of where it is placed, the microprocessor, or any other suitable processing circuitry, aids in computing the pressure in the pressure monitoring lumen 20. The information may then be stored in mass storage device 40, such as RAM, PROM, optical storage devices, flash memory devices, hardware storage devices, magnetic storage devices, or any suitable computer-readable storage medium. The information may be accessed and operated upon according to microprocessor 34 instructions. In certain embodiments, calibration information may be used in calculations for estimating of pressure in the lungs. The monitor 30 may be configured to provide indications of the lung pressure, such as an audio, visual or other indication, or may be configured to communicate the estimated lung pressure to another device, such as the ventilator 32.

The tracheal tube 12 may also include a connector 42 that communicates with monitor 30 to provide calibration information specific to the tube 12. The connector 42 may be suitably configured to connect to a receiving port on the monitor 30. The connector 42 may contain an information element (e.g., a memory circuit), such as an EPROM, EEPROM, coded resistor, or flash memory device for storing calibration information for the cuff 14. The connector may also contain certain processing circuitry for at least partially processing signals from the pressure sensor or for interacting with any memory circuitry provided. When the connector 42 is coupled to the monitor 30, the information element may be accessed to provide pressure calibration information to the monitor 30. In certain embodiments, the calibration information may be provided in a barcode that may be scanned by a reader coupled to the monitor 30. Alternatively, the pressure transducer 26 may include a passive or active RFID circuit that may be read wirelessly to convey pressure monitoring information and cuff calibration information to the monitor 30. In other embodiments, tube identifying data, calibration data, and so forth may simply be entered manually.

Figure 2:
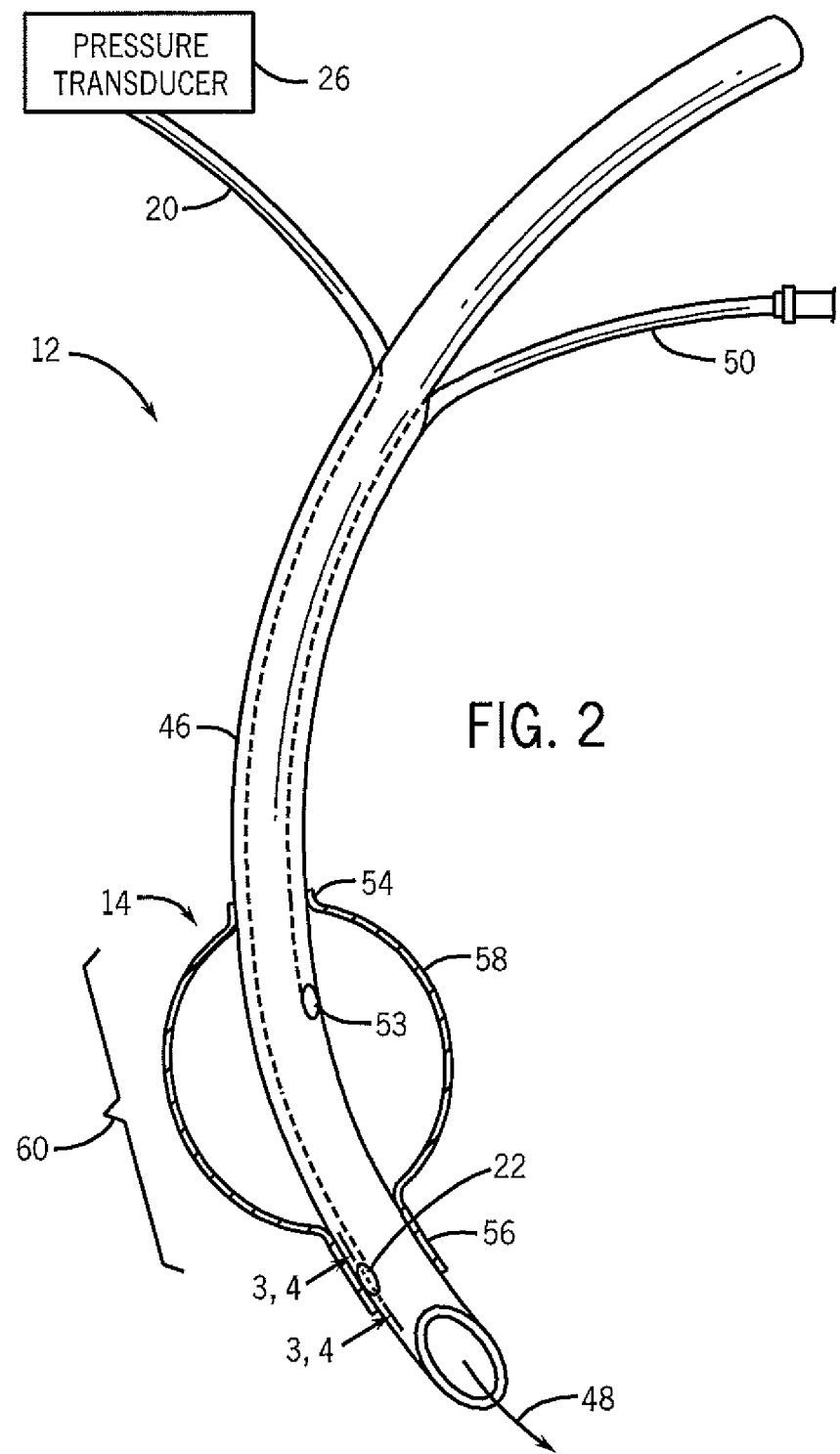
FIG. 2 is a perspective view of an endotracheal tube with a pressure monitoring lumen that may be used in conjunction with the system of FIG. 1.

FIG. 2 is a perspective view of an exemplary tracheal tube 12 according to certain embodiments. As noted, the tube 12 may include a pressure monitoring lumen 20 disposed on or in a wall 46 of the tube. The tube walls 46 define an airway flow path for delivering respiratory fluids (e.g., gases) to a patient's lungs (as shown by arrow 48) and for allowing gases to flow out of the lungs. The pressure monitoring lumen 20 may be formed in the wall of the tube and may terminate in an opening 22, which is covered by a shoulder of the cuff 14.

As noted, the tube 12 also includes an inflatable cuff 14, which may be inflated via a separate inflation lumen 50, which terminates in an opening 53 in the cuff walls between the adhesion points of the proximal cuff shoulder 54 and the distal cuff shoulder 56. The cuff walls 58 substantially enclose an inflatable region 60 around the cuff inflation opening 53, allowing the cuff 14 to be inflated when air is delivered through the inflation lumen 50.

The tube 12 and the cuff 14 may be formed from materials having suitable mechanical properties (such as puncture resistance, pin hole resistance, tensile strength), chemical properties (such as biocompatibility). In one embodiment, the walls of the cuff 14 are made of a polyurethane having suitable mechanical and chemical properties. An example of a suitable polyurethane is Dow Pellethane® 2363-80A. In certain embodiments, the cuff 14 may be formed from any suitable polyurethane-based compositions, polymethylmethacrylate, polyacrylonitrile, polyamides (such as nylon), polycarbonate, polyesters (such as polyethylene terephthalate), polyolefins (such as polyethylenes and polypropylenes), polystyrene or vinyls (such as polyvinyl chloride and polyvinylacetate). In one embodiment, the cuff 14 may be generally sized and shaped as a high volume, low pressure cuff that may be designed to be inflated to pressures between about 15 cm $H_2O$ and 30 cm $H_2O$. As noted, the cuff 14 may be substantially impermeable to respiratory gases.

The system 10 (see FIG. 1) may also include a respiratory circuit connected to the endotracheal tube 12 that allows one-way flow of expired gases away from the patient and one-way flow of inspired gases towards the patient. The respiratory circuit, including the tube 12, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene.

The inflatable cuffs 14 discussed herein may be formed by various techniques. In one implementation of the present technique, the inflatable cuff 14 is formed by blow-molding. In one example of such an implementation, a tubular polyurethane extrusion is blow-molded to form the cuff 14. The tubular extrusion has a suitable internal diameter and wall thickness such that, when the extrusion is blown, the resulting cuff 14 has a sufficient internal diameter to fit onto an endotracheal tube 12 and has the desired wall thickness. When the cuff 14 is formed by such blow-molding techniques, the walls 58 of the inflatable region 60 of the cuff 14 become thinner as the inflated diameter of the region 60 increases. Because the shoulder regions are not substantially blown out, the shoulders (e.g., proximal shoulder 54 and distal shoulder 56) may generally maintain about the same thickness as the tubular substrate. Accordingly, while the inflatable region 60 may include wall 58 that varies in thickness and grow thinner towards the midpoint of the inflatable region 60, the shoulder regions, may generally include cuff walls 58 of relatively constant thickness. Further, because the variable thickness of the walls 58 of the inflatable region, the shoulder regions of the cuff 14 may have a higher average or mean wall thickness than the inflatable region 60.

For example, a tubular substrate, such as an extruded polyurethane tube, may be loaded into a blowing machine, such as a machine used to blow angioplasty balloons, or other suitable mold assembly. In one such an embodiment, the tubular substrate, such as a polyurethane tube, may be 11 to 12 inches (27.94 cm to 30.48 cm) in length with an internal diameter between 0.235 inches and 0.245 inches (5.969 mm to 6.223 mm) and a wall thickness between 0.008 inches and 0.012 inches (0.2032 mm to 0.3048 mm). In specific embodiment, a substrate may form a cuff having a wall thickness of 0.015 mm±0.007 mm. For example, in one particular implementation a commercially available extrusion of Dow Pellethane® 2363-90A having a length of 12 inches, an inner diameter of 0.239±0.005 inches (6.0706±0.127 mm) and a wall thickness of 0.008 inches (0.2032 mm) may be blown to form a cuff 14 having a wall thickness less than or equal to 0.001 inches (0.0254 mm) suitable for use with a 7.5 mm internal diameter (ID) endotracheal tube. It should be understood that the wall thickness of some or all of the distal shoulder 56 may be altered to increase the responsiveness to pressure changes. For example, the wall thickness of at least an area of the distal shoulder 56 covering the opening 22 may be thinner than the walls of the rest of the distal shoulder 56 to increase such responsiveness.

Figure 3:
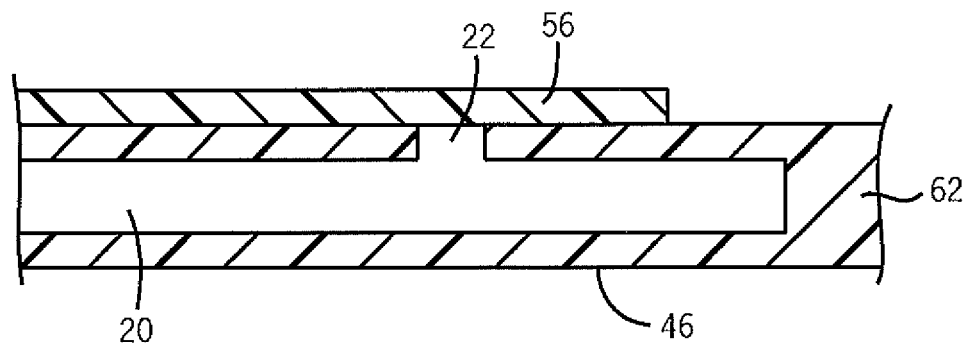
FIG. 3 is a cross-sectional view of the endotracheal along an axis of the pressure monitoring lumen.

The pressure monitoring lumen 20 may be formed within the walls 46 of the tube 12, for example by extrusion, as shown in FIG. 3, a cross-sectional view of the tube 12 along the axis of the lumen 20. The opening 22 in the tube walls 46 may be located at any position on the tube 12 distal to inflatable region 60 (see FIG. 2). Generally, the lumen 20 may be open through the most of the length of the walls 46 and may terminate at the distal end 62, where the lumen may be sealed shut, e.g., via heat-sealing. For extruded tubes 12, when the distal end 62 is cut at a slant, the distal end of the lumen 20 may be concurrently sealed. The opening 22 may be formed by cutting or forming a notch through a portion of the wall 46. While the opening 22 may be any size, its diameter may be proportional to the diameter of the lumen 22. For example, a 1 mm lumen may have an opening 3 mm in diameter. Alternatively, the pressure monitoring lumen 20 may be a separate structure that is adhered to or otherwise associated with the tube 12 prior to insertion. In such embodiments, the opening 22 may be preformed at an appropriate location.

The opening 22 may be located on the tube 12 such that a commercially available cuff 14 with standard shoulder lengths may completely cover the opening 22. Generally, cuffs 14 may be slid onto the tube 12 and subsequently adhered (e.g., by injecting an adhesive under the shoulders once the cuff is in place (e.g., proximal shoulder 54 and distal shoulder 56). Proper placement of the cuff 14 with respect to the cuff inflation opening 53 may also ensure covering of the pressure monitoring lumen opening 22. In other embodiments, the opening 22 may be located more distally on the tube 12, such that the distal shoulder of the cuff 14 may be longer than the proximal shoulder 54 to extend down the length of the tube 12 to cover the opening 22. Generally, the distal shoulder 56 may not cover a Murphy eye, typically located adjacent to the distal end 62 of the tube 12. However, the distal shoulder may be irregularly shaped to avoid the Murphy eye. For example, the distal shoulder 56 may include distal tab extensions to cover the opening 22 that do not also cover the Murphy eye.

Figure 4:
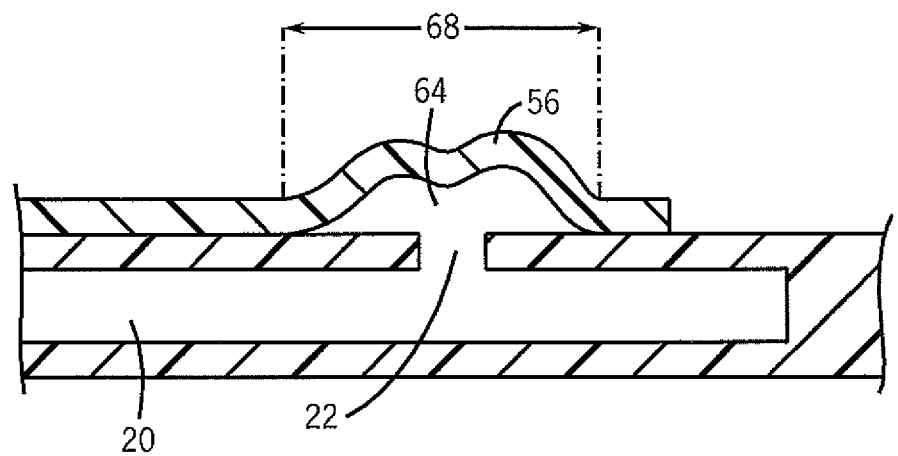
FIG. 4 is an alternative cross-sectional view of the endotracheal along the axis of the pressure monitoring lumen.

FIG. 4 is a cross-sectional view of an alternative arrangement of the distal shoulder 56 covering the opening 22. As shown, the distal shoulder may be folded or loose across the opening 22, creating a small gap 64 cross-sectional view of the tube 12 along the axis of the lumen 20. In certain embodiments, air or other fluids may be transferred into the lumen 20 to at least partially inflate the loose or folded region of the distal shoulder. In such an embodiment, the cuff 14 may include a first inflatable region 60 and a second inflatable region 68, the second inflatable region 68 being formed within the distal shoulder 56. In this case, the trachea pressure determination may be similar, but may involve different calibration functions to account for the volume of the inflated region 68 on the pressure. The second inflatable region 68 may be formed by allowing some slack in the distal shoulder 56 during the cuff adhesion process. Alternatively, the second inflatable region 68 may be blow molded in a manner similar to the blow molding process for the inflatable region 60.

Figure 5:
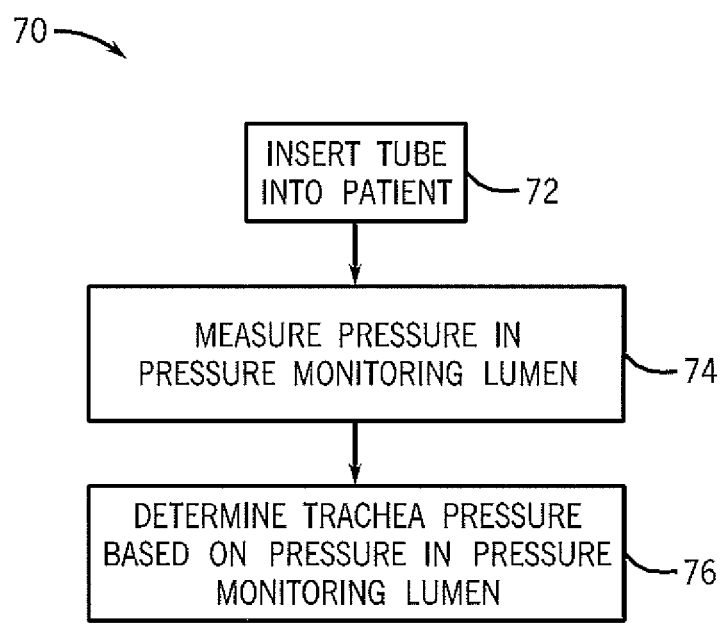
FIG. 5 is a flow diagram of an exemplary method for monitoring tracheal pressure.

FIG. 5 is a process flow diagram illustrating a method for determining tracheal pressure in conjunction with tracheal tubes and systems as provided. The method is generally indicated by reference number 70 and includes various steps or actions represented by blocks. It should be noted that the method 70 may be performed as an automated procedure by a system, such as system 10. Further, certain steps or portions of the method may be performed by separate devices. For example, a first portion of the method 70 may be performed by a caregiver, while a second portion of the method 70 may be performed by a monitor 30. In embodiments, the method 70 may be performed continuously or intermittently for long-term patient monitoring or at any appropriate interval depending on the particular situation of the intubated patient.

In certain embodiments, the method 70 begins with insertion of the tube 12 into the patient at step 72. At step 74, a pressure transducer 26 in fluid communication with the lumen 20 may provide pressure readings of the pressure monitoring lumen to a connected device, such as a monitor 30. The monitor 30 may perform analysis of the pressure readings at step 76. In certain embodiments, the monitor may apply a correction factor to the pressure readings in determining the tracheal pressure. The correction factor may be determined empirically, and may be stored in the connector 42 or the monitor 30. The correction factor may account for certain effects of the cuff material, the shape of the opening 22, or the looseness or tautness of the distal shoulder 56 over the opening 22 on the pressure readings. For example, the trachea pressure may be determined from the pressure inside the pressure monitoring lumen 20 as provided in U.S. patent application Ser. No. 12/477,636 to Sarah Hayman et al., filed on Jun. 3, 2009. The trachea pressure may be displayed or otherwise further processed to determine if the inner diameter of the tube 12 has decreased, and/or to change the settings on the ventilator 32.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of tracheal pressure, but these techniques may also be utilized for the measurement and/or analysis of the surrounding pressure for any medical device inserted into a patient's airway. Rather, the various embodiments may cover all modifications, equivalents, and alternatives falling within the spirit and scope of the disclosure as defined by the following appended claims.

What is claimed is:

1. A tracheal tube comprising:
a conduit capable of transferring a fluid to a patient's lungs;
an inflatable cuff associated with the conduit, the inflatable cuff comprising an inflatable region, a distal shoulder, and a proximal shoulder;
a first lumen disposed in a wall of the conduit, wherein the first lumen is capable of inflating a portion of the inflatable cuff through a first opening in the wall of the conduit; and
a second lumen disposed in the wall of the conduit, wherein the second lumen comprises a second opening in the wall of the conduit, and wherein the second opening is covered by the distal shoulder of the cuff.

2. The tracheal tube of claim 1, comprising a memory circuit storing data representative of a relationship between a pressure in the lumen and a *trachea* pressure.

3. The tracheal tube of claim 2, wherein the memory circuit is associated with a connection or cable on the tracheal tube.

4. The tracheal tube of claim 1, comprising a pressure transducer in fluid communication with the second lumen.

5. The tracheal tube of claim 1, wherein the distal shoulder is longer along an axis of the conduit than the proximal shoulder.

6. The tracheal tube of claim 1, wherein the second lumen is sealed, such that when a pressure is exerted on a portion of the distal shoulder covering the second opening, a pressure inside the second lumen increases.

7. The tracheal tube of claim 6, wherein the second lumen is filled with a gas.

8. The tracheal tube of claim 1, wherein a portion of the distal shoulder covering the second opening is substantially loose about the opening and capable of being at least partially inflated.

9. The tracheal tube of claim 1, wherein the distal shoulder is substantially taut over the second opening.

10. The tracheal tube of claim 1, wherein the distal shoulder comprises a higher average wall thickness than the inflatable region of the cuff.

11. A system for determining trachea pressure comprising:
a tracheal tube, the tracheal tube comprising:
a conduit comprising a distal end and a proximal end, wherein the conduit is capable of transferring a fluid to a patient's lungs;
a pressure monitoring lumen disposed in a wall of the conduit, wherein the pressure monitoring lumen comprises an opening in the wall of the conduit, and wherein the opening is proximal to a distal end of the pressure monitoring lumen;
an inflatable cuff associated with the conduit, the inflatable cuff comprising a distal shoulder and a proximal shoulder, wherein a portion of the distal shoulder covers the opening;
a pressure transducer in fluid communication with the lumen; and
a processor configured to determine a trachea pressure based upon a signal from the pressure transducer.

12. The system of claim 11, comprising an information element associated with the tracheal tube, wherein the information element comprises stored data representative of a relationship between a pressure in the pressure monitoring lumen and a trachea pressure.

13. The system of claim 11, wherein the distal shoulder is longer along an axis of the conduit than the proximal shoulder.

14. The system of claim 11, wherein the pressure monitoring lumen is sealed, such that when a pressure is exerted on a portion of the distal shoulder covering the opening, a pressure inside the pressure monitoring lumen increases.

15. The system of claim 11, wherein the pressure monitoring lumen is filled with a gas.

16. The system of claim 11, wherein a portion of the distal shoulder covering the second opening is substantially loose about the opening and capable of being at least partially inflated.

17. The system of claim 11, wherein the distal shoulder is substantially taut over the opening.

18. The system of claim 11, wherein the distal shoulder comprises a higher average wall thickness than an inflatable region of the cuff.

19. A method of manufacturing a tracheal tube comprising:
   providing a conduit comprising a distal end and a proximal end, wherein the conduit is capable of transferring a fluid to a patient's lungs;
   providing a lumen disposed in a wall of the conduit, wherein the lumen comprises an opening in the wall of the conduit adjacent to the distal end;
   providing an inflatable cuff comprising a distal shoulder and a proximal shoulder; and
   applying the inflatable cuff to the conduit such that the opening is covered by the distal shoulder of the inflatable cuff.

20. The method of claim 19, wherein applying the inflatable cuff to the conduit comprises leaving a portion of the distal shoulder adjacent to the opening unattached to the conduit.

21. The method of claim 19, wherein applying the inflatable cuff to the conduit comprises applying an adhesive to the distal shoulder to adhere the distal shoulder to the conduit.

* * * * *